United States Patent [19]

Böttger

[11] 4,213,456

[45] Jul. 22, 1980

[54] MEDICAL MULTI-PURPOSE INSTRUMENT

[76] Inventor: Paul E. K. Böttger, Bahnhofstrasse 35, 6050 Offenbach, Fed. Rep. of Germany

[21] Appl. No.: 853,381

[22] Filed: Jan. 30, 1978

[30] Foreign Application Priority Data

Jan. 7, 1978 [DE] Fed. Rep. of Germany ....... 2800659

[51] Int. Cl.² .......................................... A61M 5/315
[52] U.S. Cl. ............................... 128/218 P; 128/234; 128/763
[58] Field of Search ......... 128/218 P, 218 PA, 218 R, 128/221, 220, 215, 216, 234, 760, 763, 765; 222/386, 386.5

[56] References Cited
U.S. PATENT DOCUMENTS

| 2,602,447 | 7/1952 | Kollsman | 128/218 P |
| 2,708,438 | 5/1955 | Cohen | 128/220 |
| 2,812,763 | 11/1957 | Ferguson | 128/218 R |
| 2,902,995 | 9/1959 | Loper | 128/215 |
| 3,128,765 | 4/1964 | Tint | 128/218 R |
| 3,545,607 | 12/1970 | Keller | 128/218 P X |
| 3,845,762 | 11/1974 | Cloyd | 128/218 P |

*Primary Examiner*—John D. Yasko
*Attorney, Agent, or Firm*—W. G. Fasse; D. F. Gould

[57] ABSTRACT

The present medical instrument includes but three basic parts, namely an outer cylinder, an inner cylinder, and a cap. These parts are so constructed that the same cap type can close at least one end of the outer cylinder and both ends of the inner cylinder whereby the latter may be operated as a piston inside the outer cylinder. Thus, the instrument is usable as a syringe and/or as a container.

14 Claims, 18 Drawing Figures

MEDICAL MULTI-PURPOSE INSTRUMENT

BACKGROUND OF THE INVENTION

The invention is a multi-purpose medical instrument, which may be employed selectively for various purposes.

The disposable syringes commonly used in the medical field are not only suitable for medical injections, but are also used for taking medical specimens, such as blood.

This medical specimen is often not examined on the spot, but is sent, sometimes even by mail, to another institute or laboratory. For this purpose, the medical specimen is usually transferred from the extracting syringe to a preferably sterilized mailing tube at the place where the specimen was obtained. During this procedure, the specimen, blood, for instance, is subjected to pressure and substantial agitation. Furthermore, this procedure is carried out under open conditions, i.e. under the influence of air, whereby material may easily be spilled. Consequently, there is a danger of infection for the technician, bacteriologist, and others handling the material, and the medical specimen may become contaminated.

OBJECTS OF THE INVENTION

It is the aim of the invention to achieve the following objects singly or in combination:
- to transform a disposable syringe into a multi-purpose instrument for medical use: for injections and for taking blood or other medical specimens—as is possible with conventional syringes—to subsequently use the same syringe as a container for transporting or mailing the specimen obtained;
- to combine the individual components of this multi-purpose instrument for various purposes so that it may be pre-filled with medicaments, chemical reagents, mediums, surgical material such as sutures, ointments, lubricating jelly, oil, etc. whatever item may be tolerated by plastic material; and
- to construct the syringe/container instrument from three basic components of which one is capable of three different functions.

SUMMARY OF THE INVENTION

Such a medical multi-purpose instrument, which comprises a cylindrical tube with a needle socket bearing a cap and a plunger with a detachable piston, is characterized in that the cylindrical tube has a concentrical ring rim with a screw thread; the hollow plunger has a screw thread at its closed end as well as at its open end; the needle socket of the cylindrical tube, as well as both ends of the plunger, are each fitted with a shaped part acting as a piston or cap; the diameter of the shaped part corresponds with the inside diameter of the cylindrical tube. The shaped part has a discoid flange and a concentrical ring rim on one side of the flange with an internal screw thread, and, if need be, with an external screw thread.

The present multi-purpose instrument thus comprises three fundamental elements: a cylindrical tube with a needle socket, a hollow plunger and finally three identical parts, which perform a double function, firstly as a piston in the cylindrical tube and secondly as a cap for the cylindrical tube and plunger.

Due to the special structure of this medical multi-purpose instrument, numerous advantages occur in its construction, manufacture and in its practical clinical use, which are described as follows.

When the instrument according to the invention was first conceived, it was taken into account that the physician or nurse would always have the choice of using it as a syringe in the traditional way and also as a container for the medical speciment obtained, should transportation or mailing of such specimen be necessary. For example, after use of the instrument as an injection syringe, it is constructed so that the hollow plunger may be unscrewed and also used as a mailing tube. This feature also applies when using the cylindrical tube as a container for blood or urine as test material, whereby the hollow plunger, mailing tube, does not contact the blood or urine. For instance, it is particularly practical for a doctor when on a house call or in a ward of a hospital if he can use the multi-purpose instrument to transport blood or urine as test material, instead of having to take along an extra mailing tube for the same purpose.

The simple structure of this medical multi-purpose instrument, comprising only three fundamental elements with an exchangeable piston and cap for use as required, has a favourable effect on the production of this instrument. As they are designed to perform the same and different functions, fewer parts, which will be discarded later anyway, have to be produced and less pollution will result.

Due to the multiple functions of the medical multi-purpose instrument and its parts, the storage space required for the bulk material will be considerably reduced by about 50%.

In comparing the present instrument to the prior art with regard to the manufacture of the multi-purpose instrument, about 40% to 50% fewer plastic moulds will be required compared with the number of plastic moulds required for the production of disposable syringes and different types of plastic containers heretofore used to carry or mail medical specimens. Thus in the manufacturing process, work at the assembly line will be facilitated and less costly. Now only one single plastic mould will be necessary for making the cap member which is constructed for three different functions, namely closing the outer cylinder at the needle socket and inside thereof, closing one or both ends of the inner cylinder, and operating as a piston inside the outer cylinder.

Finally, due to the exclusive use of polyethylene, polypropylene or polystyrene or other thermo-plastics, the basic conditions for recycling the used items of the multi-purpose instruments are fulfilled.

BRIEF FIGURE DESCRIPTION

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figures 1, 1A:
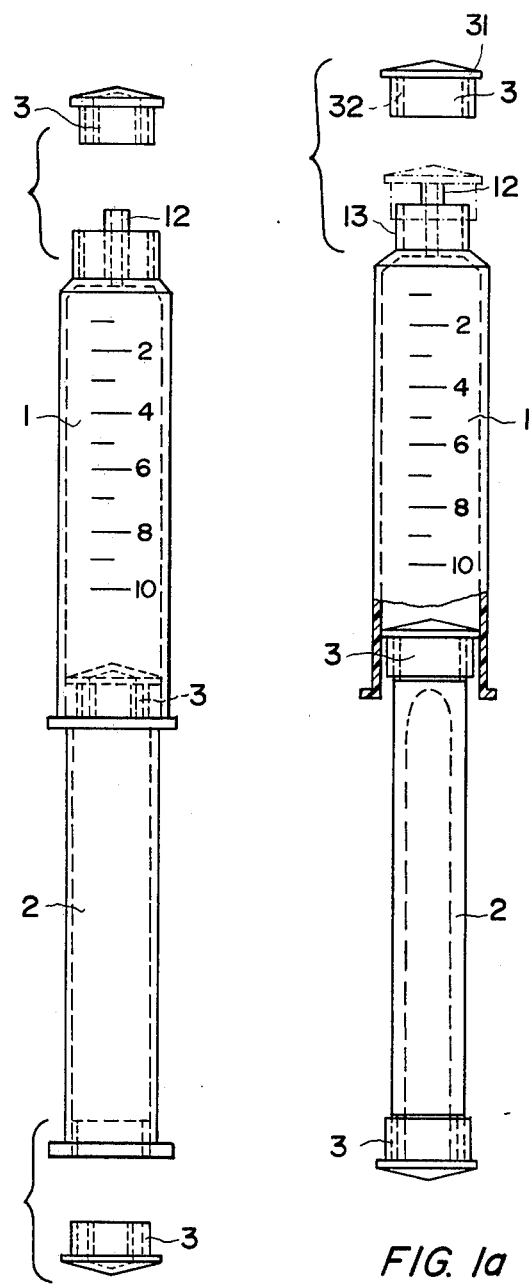
FIG. 1 shows a side view of the present medical multi-purpose instrument with its three fundamental elements.
FIG. 1a shows the multi-purpose instrument constructed in a more simplified form.

According to FIG. 1, the medical multi-purpose instrument comprises a hollow cylindrical outer tube 1, a hollow inner cylindrical tube or cylinder 2 and three shaped cap members 3, functioning as a cap for the cylindrical tube 1 as well as for the inner cylinder 2 and as a piston inside the cylindrical tube 1. All three cap members are substantially identical to each other.

Figure 2:
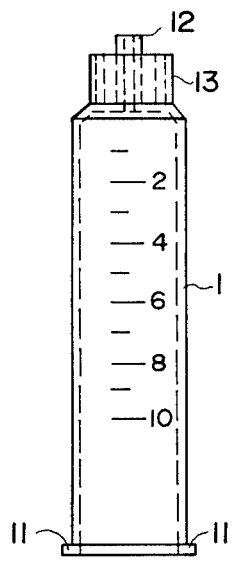
FIGS. 2 to 4 show the elevational, sectional, and bottom view of the first, outer cylindrical tube.
Figure 3:
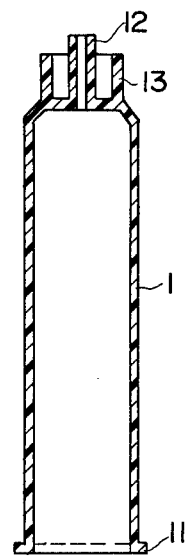
Figure 4:
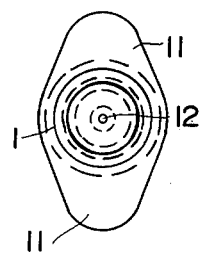

According to FIGS. 2 to 4, the cylindrical tube 1—preferably made of transparent plastic material—has two extensions 11 located diametrically opposite each other at its open end. At the other, closed end, a needle socket 12 is provided and a ring rim or bushing 13 fitted concentrically relative to the needle socket 12. The ring rim 13 is provided with an internal screw thread, into which the external screw thread of the respective cap member 3 may be screwed.

Figure 14:
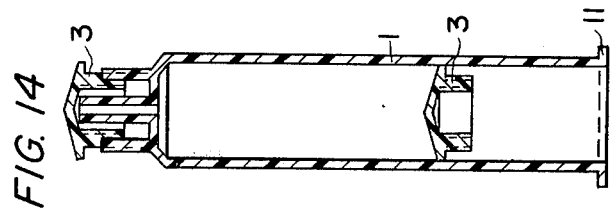
FIGS. 11 to 14 show examples of the different uses of the first, outer cylindrical tube.
Figure 13:
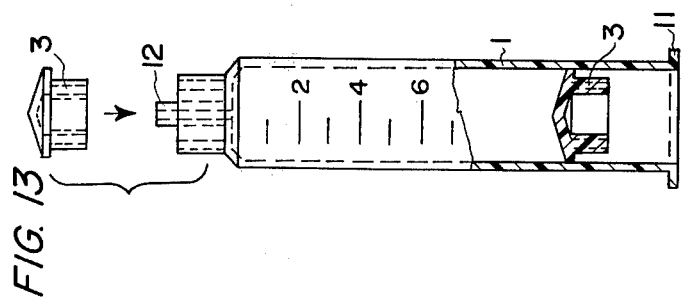

As may be seen from FIGS. 13 and 14 in particular, the needle socket 12 and the ring rim 13 are preferably so constructed that the cap member 3 causes a double closing effect. This is achieved in a practical way by making the needle socket 12 of the cylindrical tube 1 long enough to extend axially out of the ring rim 13 as shown in FIGS. 2 and 3.

Figure 5:
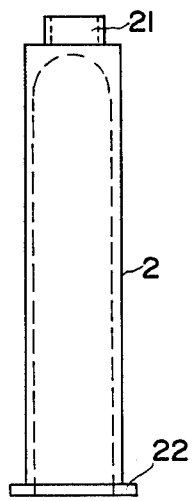
FIGS. 5 to 7 show the elevational, sectional, and bottom view of the second, inner cylindrical tube.
Figure 6:
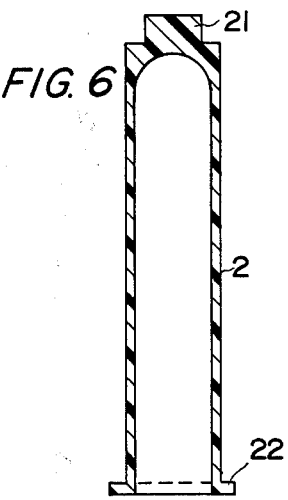
Figure 7:
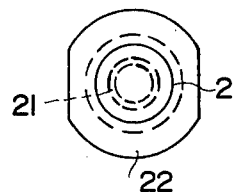

According to FIGS. 5 to 7, one end of the inner cylinder 2 acting as a plunger and likewise made of transparent plastic material, is closed and fitted with a coaxial lug 21 having an external screw thread in order to connect a cap member 3 as a piston to the cylindrical plunger 2.

At the open end of the plunger 2, there is an annular flange 22, which is appropriately cut-off at diametrically opposite sides (FIG. 7), thus allowing the alignment of the stationary bow shaped portions of the annular flange 22 with the extensions 11 of the cylindrical tube 1. The annular flange can also be left in its circular shape, in which case a cap with internal screw thread can be attached for better closure of the hollow plunger 2 when used as a mailing tube.

Figure 8:
FIGS. 8 to 10 show the elevational, sectional, and bottom view of the cap member.
Figure 9:
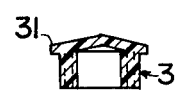
Figure 10:
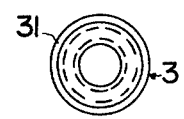

As may be seen from FIGS. 8 to 10, the cap member 3 has a discoid component 31 as well as a ring or bushing rim 32 placed coaxially on one side of the discoid component and forming an integral structure with the disk 31. This ring rim 32 has an external screw thread for the ring rim 13 of the cylindrical tube 1 and an internal screw thread for the lug 21 of the plunger 2.

The outside diameter of the discoid part 31 corresponds to the inside diameter of the cylindrical tube 1. The cap member 3, which is screwed onto the lug 21 of the plunger 2 may serve as a piston in the cylindrical tube 1 or as a cap at the open end of the cylindrical tube 1 after the plunger 2 has been unscrewed (FIG. 14).

Figure 17:
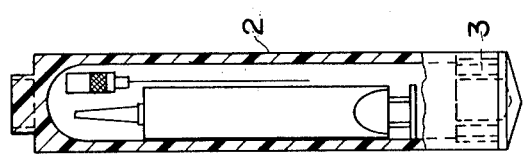
FIGS. 15 to 17 show examples of the different uses of the second, inner cylindrical tube.
Figure 16:
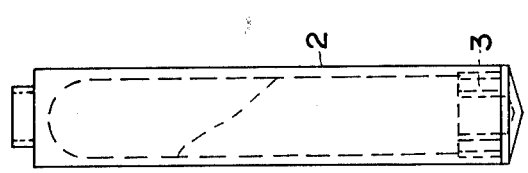
Figure 15:
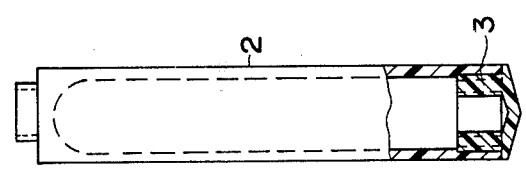

A second shaped cap member 3 acts as a closure for the plunger 2 by being inserted with its ring rim 32 into the open end of the plunger 2 (FIGS. 15, 16, and 17).

Finally, as already mentioned, a third shaped cap member 3 is used as a closure for the needle socket 12 of the cylinder tube 1.

The discoid part 31 of the screw cap member 3 may have a flat exterior in its simplest form. Preferably, however, as shown in FIGS. 8 to 10, the exterior of the discoid part 31 should be cone shaped.

According to preferred modifications of the invention shown in FIG. 1a, the shaped cap member 3 is constructed in an even simpler form. The ring rim 32 forming one piece with the discoid part 31 has only an internal screw thread. A medical multi-purpose instrument with such a shaped cap member 3 has, as is clearly visible from FIG. 1a, a plunger 2 with an external screw thread at both its closed and open end to screw on the shaped cap member 3 to serve as either a piston or a cap.

In this case the plunger 2 does not require any central lug 21 at its closed end, nor any annular flange 22, nor any internal screw thread at its open end. Rather the external screw thread at both ends of the plunger 2 is sufficient. In this type of structure the internal screw thread of the ring rim 32 of the shaped cap 3 corresponds to both the internal screw threads at both ends of the hollow plunger 2 and appropriately also to the external screw thread of the ring rim 13 of the cylindrical tube 1 surrounding the needle socket 12. The discoid part 31 of the shaped cap member 3 serves in turn as a closure for the open end of the plunger 2 which now, for example, can serve as a mailing tube. Attached to the closed end of the plunger 2 the disk 31 serves actually as a syringe piston in the conventional sense. After extracting blood or urine, the shaped cap member 3, which surrounds the closed end of the plunger 2 as a fitted outer cap, may be unscrewed from the plunger and left in the cylindrical tube 1, where it then serves as an inner cap for the cylindrical tube 1, which is thus transformed into a container for test material. After being disconnected from the shaped cap 3, which served as a piston, the plunger 2, which was not contaminated by the described extraction of a specimen, can be kept, for instance, for later use of the hollow plunger as a mailing tube. By screwing the shaped cap 3 with its internal screw thread onto the ring rim 13, which now has an external screw thread, and which surrounds the needle socket 12 on the cylindrical tube 1, a sealing function is likewise performed by the disk 31. The advantages of the modifications as shown in FIG. 1a, lie in the production as well as in the use of the instrument. The ring rim 32 of the shaped cap 3 requires only an internal screw thread, whereby expensive injection moulding techniques for a second screw thread size is rendered superfluous.

The shaped cap 3 may thus, where necessary, be screwed onto all parts of the instrument in the same manner, in order to serve as a fitted outer cap in all three positions. This simplification of the instrument makes it easier for the doctor or nurse to handle the same.

Instead of the threaded joint between the shaped cap 3 and the plunger 2, the shaped part serving as a piston, may also be designed as a plug and screw connection, e.g. like a bayonet socket. For this purpose, the internal screw thread of the ring rim 32 may only be half-finished towards the underside of the disk 31, whereby a plug and screw connection is formed.

As with the usual disposable syringe, a needle cover not shown may also be utilized.

The needle cover may be rounded off at both ends and have an internal screw thread. By using the multi-purpose instrument with such a needle cover, urine may be obtained under closed and sterile conditions. For this purpose, the needle cover is screwed onto the needle socket 12 and inserted into the urethra to obtain a urine sample. Following this procedure, the needle cover is replaced by the cap member 3.

In practice, due to the unvaried form of the three basic elements of the present medical multi-purpose instrument, it may be used for different purposes, as follows.

Figure 12:
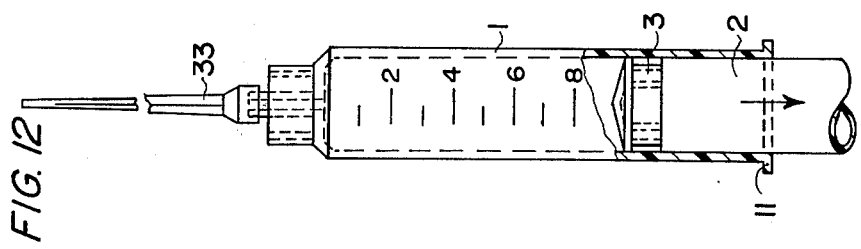
Figure 11:
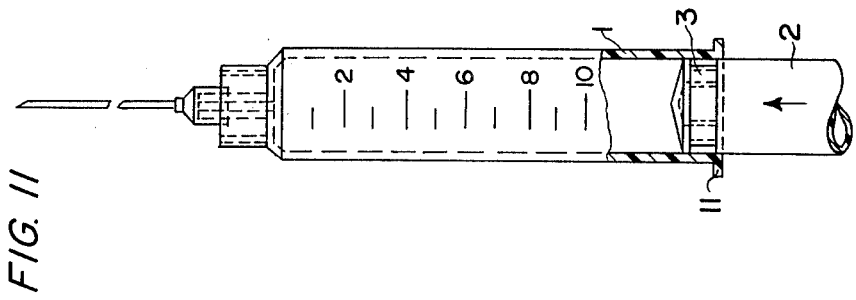

The cylindrical outer tube may be used:

(1) as part of a disposable syringe thereby forming the cylindrical tube of an injection syringe, FIG. 11;

(2) as a container for a medical specimen, FIG. 13, FIG. 14;

(3) as a catheter or aspirator instrument with a needle cover but without a needle attached or a flexible tube or cannula 33, FIG. 12;

(4) as a container for surgical suture material, whereby the surgeon can stitch when holding this instrument in his hand;

(5) as a pre-manufactured vacuum container, to obtain blood, water, urine, or any other fluids or gas for examination;

(6) as a pre-manufactured pressurized container; and (7) as an outside case, by attaching two cylindrical tubes 1 to each other at the base, for example by a ¼ turn, or by a winglike cut in the material at the finger grip, i.e. at the extensions 11 of each cylindrical tube, whereby the so-formed outside case serves as a protection for the inner tube plunger 2, e.g. a 10 ml inner tube.

The inner cylindrical or plunger 2 may be used:

(1) as a piston for the injection syringe, FIG. 11;

(2) as a laboratory and mailing tube, FIG. 15;

(3) as a case for an insulin syringe to incorporate the needle and injection material after self-injection with insulin, FIG. 17, in order to avoid pollution, accidents or misuse by others;

(4) as a culture tube, e.g. for screening bacteria of the urinary tract. This tube conforms to the German Industrial Standards (DIN) due to its water-tight cap, outside case-mailing tube and size, FIG. 16;

(5) as a container for formalin and for transporting cell tissue, FIG. 15; and (6) as a container for specimens and chemical reagents, FIG. 15.

The shaped cap member may be used:

(1) as a piston, which, after being disconnected from the plunger, remains in the cylindrical tube as the sealing cap so that the cylindrical tube may be used as a container, FIG. 12;

(2) as a cap for the needle socket of the syringe, FIG. 13, FIG. 14; and (3) as a cap for the plunger when used as a laboratory and/or mailing tube, FIG. 15.

The invention must not necessarily be constructed in the specific way described. Details may be changed and adapted to a respective purpose without deviation from the principle idea of the invention. This also particularly applies when using the cylindrical tube as a container, not only for medical or other specimens, but also for experiments and chemical reagents—even after its use as part of a syringe.

Although the invention has been described with reference to specific example embodiments, it will be appreciated that it is intended to cover all modifications and equivalents within the scope of the appended claims.

I claim:

1. A multipurpose medical instrument, comprising first hollow cylinder means having a given inner diameter, a needle socket and first cap holding means surrounding said needle socket at one end of said first hollow cylinder means and an open end opposite said needle socket of said first hollow cylinder means, second hollow cylinder means operable as a plunger inside said first hollow cylinder means and having further cap holding means at each end of said second hollow cylinder means, said further cap holding means and said first mentioned cap holding means being of substantially identical construction, and a plurality of cap means all of which are also of substantially identical construction for cooperation with any of said cap holding means, said cap means having an outer diameter substantially corresponding to said given inner diameter of said first hollow cylinder means whereby one of said cap means at one end of said second hollow cylinder means may function as a piston inside said first hollow cylinder means while other cap means function as closure means.

2. The instrument of claim 1, wherein said first hollow cylinder means comprise at said open end thereof two extensions (11) located substantially diametrically opposite each other, said cap holding means (13) of said first hollow cylinder means comprising a bushing concentrically surrounding said needle socket (12) said bushing being adapted to hold one of said cap means.

3. The instrument of claim 2, wherein said bushing comprises threading means, said cap means comprising corresponding threading means for cooperation with said threading means of said bushing.

4. The instrument of claim 1, wherein said first mentioned cap holding means and said needle socket are so constructed and arranged relative to each other that the respective cap means seals the needle socket in the closing position of the respective cap means when the latter is secured to said first mentioned cap holding means.

5. The instrument of claim 1, wherein said one end of said second hollow cylinder means is closed, said further cap holding means at said one closed end comprising an axially positioned stud constructed to secure the respective cap means to said closed end of the second hollow cylinder means for said piston function of said respective cap means.

6. The instrument of claim 5, wherein said axially positioned stud comprises an outer threading to form said holding means, said cap means having an inner threading for cooperation with said outer threading of said stud.

7. The instrument of claim 1, wherein said second hollow cylinder means comprises at least one open end and a ring flange (22) secured to said open end of said second hollow cylinder means.

8. The instrument of claim 7, wherein said ring flange has cut-off rim segments located substantially opposite each other.

9. The instrument of claim 1, wherein each of said cap means comprises a circular disk and a bushing coaxially secured to said circular disk on one side of the circular disk.

10. The instrument of claim 9, wherein said bushing of said cap means comprises an inner threading and an outer threading.

11. The instrument of claim 9, wherein said circular disk has an outer diameter corresponding to said given inner diameter of said first hollow cylinder means.

12. The instrument of claim 9, wherein said second hollow cylinder means has a given inner diameter, said bushing having an outer diameter corresponding to said given inner diameter of said second hollow cylinder means.

13. The instrument of claim 1, further comprising an elongated tubular member having a first end adapted for connection to said needle socket, said tubular member having a second free end and a diameter which becomes smaller from said first end to said second end for taking urine samples.

14. The instrument of claim 1, wherein said cap means comprise three substantially identical cap members.

* * * * *